(12) United States Patent
Papirov (10) Patent No.: US 11,229,387 B2
(45) Date of Patent: Jan. 25, 2022

(54) DEVICE, SYSTEM AND METHOD FOR URINARY BLADDER FULLNESS INDICATOR (71) Applicant: Eduard Papirov, Hod Hasharon (IL)

(72) Inventor: Eduard Papirov, Hod Hasharon (IL)

(*) Notice: Subject to any disclaimer, the term of this patent is extended or adjusted under 35 U.S.C. 154(b) by 741 days.

(21) Appl. No.: 16/098,210

(22) PCT Filed: May 1, 2017

(86) PCT No.: PCT/IL2017/050486
§ 371 (c)(1),
(2) Date: Nov. 1, 2018

(87) PCT Pub. No.: WO2017/191633
PCT Pub. Date: Nov. 9, 2017

(65) Prior Publication Data
US 2019/0142324 A1  May 16, 2019

(30) Foreign Application Priority Data

May 1, 2016 (IL) ......................................... 245371

(51) Int. Cl.
*A61B 5/20* (2006.01)
*G01F 23/296* (2006.01)
*A61B 5/00* (2006.01)
*G01F 23/28* (2006.01)
*G01F 23/00* (2006.01)

(52) U.S. Cl.
CPC ............ *A61B 5/204* (2013.01); *A61B 5/0028* (2013.01); *A61B 5/0051* (2013.01); *A61B 5/20* (2013.01); *G01F 23/00* (2013.01); *G01F 23/28* (2013.01); *G01F 23/296* (2013.01); *A61B 2562/0204* (2013.01)

(58) Field of Classification Search
None
See application file for complete search history.

(56) References Cited

U.S. PATENT DOCUMENTS

| 6,579,247 B1 * | 6/2003 | Abramovitch | A61B 5/204 600/438 |
| 8,221,337 B2 * | 7/2012 | Companion | A61B 8/08 600/587 |

* cited by examiner

Primary Examiner — Amelie R Davis
Assistant Examiner — Marjan Saboktakin
(74) Attorney, Agent, or Firm — The Law Office of Joseph L. Felber (57) ABSTRACT A bladder volume detection device, the device comprising a sound transmitter and at least one receiver the device configured to ping the bladder with an acoustic signal having a resonant frequency of up to about 20 k Hz generated with said transmitter.

17 Claims, 9 Drawing Sheets

DEVICE, SYSTEM AND METHOD FOR URINARY BLADDER FULLNESS INDICATOR

FIELD OF THE INVENTION

The present invention relates to a device, system and a method for detecting the fullness of the urinary bladder.

BACKGROUND OF THE INVENTION

The urinary bladder functions to collects and stores urine produced by the kidneys. The urinary bladder received urine from the kidney via the upper ureters, where it is stored until it is urination. The urinary bladder excretes the urine via the urethra. Excretion of urine from the urinary bladder is a controlled function based on the concerted activity of the bladder muscles and the urinary sphincters. Control over the muscles along the urinary path from the bladder to the urethra is termed continence while lack of control of the urinary pathway is referred to as incontinence. For purposes herein the inability of the body to control the discharge of urine is termed incontinence.

Incontinence, may be due to various reasons with a variety of origins usually either relating to at least one or a combination of neurological origins and/or physiologic origins. An example of physiologic original is seen in women in the form of poor muscle tone of the pelvic floor, leading to incontinence. In men, incontinence problems are usually associated with the prostate gland where urinary retention issues are usually due to or associated with the prostate gland itself.

Urodynamic testing produces graphical and numerical data that record the test data to provide that may be further analyzed allowing a practitioner to diagnose and attempt to identify and categorized the problem while attempting to define a potential remedy. Urodynamic testing is generally provided in a clinical setting which at times may be problematic for some individuals.

Urodynamic evaluations are employed to obtain quantitative data regarding the bladder. In general urodynamic testing depicts the relationship of bladder pressure to volume of contained fluid, bladder capacity, bladder compliancy (the ability of the bladder to accommodate increasing volumes), bladder pressure during urination (pressure/flow study) and times under different conditions.

Urodynamic studies are generally uncomfortable and invasive procedures that may require both urinary bladder emptying and filling studied to be carried out under laboratory conditions. Current urodynamic uroflowmetry studies require the use of urinary catheters and urination under varying conditions. Therefore such testing subjects a patient to a generally stressful and non-optimal conditions.

SUMMARY OF THE INVENTION

One solution to try to assist individuals suffering from incontinence or other bladder related disorders is to provide them with an indicator of the level of fullness of the urinary bladder. Such an indication that is provided directly to the subject and/or to a caregiver may be utilized to gain control over the bladder of a subject suffering from various bladder disorders. In particular a device capable of providing urinalysis and/or urodynamic studies in a minimally invasive manner would be advantageous.

Embodiments of the present invention provide a method and device that determines and provides an indication of the level of urinary bladder fullness or empty. The device may be used for a human or an animal subject.

Embodiments of the present invention provide for assessing the level of urinary bladder fullness by generating a soundwave in the vicinity of the urinary bladder such that the generated soundwave produces an echo reflective of the level of fullness of the urinary bladder, wherein the echo is undergoes analysis to determine the level of urinary fullness. Most preferably the generated acoustic signal is provided at a frequency of up to 20 kHz and is therefore not considered an acoustic ultrasound signal.

Embodiments of the present invention provide a device and/or system for producing a resonating percussion signal of the urinary bladder reflective of and/or parallel to the percussion sounds produced during manual finger tapping of the urinary bladder along the abdominal surface.

Embodiment of the present invention may provide for analyzing percussion sounds of various organs within the upper torso and/or abdomen for example including but not limited to any organ and/or organ system, in particular the bladder to determine the status and state of the organ being tapped by way of percussion.

Embodiments of the present invention provide for percussion assessment of the urinary bladder utilizing a device having a piezoelectric percussion and/or sound generating module and a sound detecting module for example in the form of a microphone, provided for detecting the echo produced and/or generated by the pinged organ, preferably the urinary bladder. Preferably, the device further comprising a processing module configured to analyze the generated sound signal in relation to the detected return echo signal to determine the level of fullness and/or the liquid volume of the urinary bladder.

The device and method according to the present invention provides for assessing the level of urinary bladder fullness by analyzing and/or processing soundwaves having a frequency of up to about 20 kHz and more preferably a frequency of up to about 20 kHz. Most preferably the sound wave analysis and/or processing includes emitting a sound wave in the selected frequency range toward the urinary bladder and detecting and reflected and/or refracted soundwaves returning from the bladder to indicated the level of fullness.

In embodiments, the level of fullness is indicated by the level of urinary bladder distention.

In some embodiments the sound wave received from the urinary bladder is processed and/or analyzed with a processor and/or a processing module. Optionally the processor may be internal to the device. Optionally the processor may be an external and/or auxiliary and/or remote processing device, for example including but not limited to a computer, mobile communication device, cloud based processing device, server, network computer or the like communication and processing device, or any combination thereof.

The device including a sound wave transmitter and receiver configured to emit and sense sound waves having a frequency below 20 kHz and more preferably up to about 20 kHz. Most preferably the device and/or system according to some embodiments of the present invention is placed external to the user preferably along a portion of the anatomy overlying the urinary bladder so as to place the device in proximity thereto, facilitating sound transmission and receiving (pickup).

The device may be placed in a housing conducive for placement externally over a portion of the body corresponding to and/or overlying the urinary bladder.

In some embodiments the device may feature a housing having an adhesive pad more preferably a biocompatible adhesive or glue so as to allow for securely affixing the device onto a user's body over a portion overlying the bladder.

In some embodiment the device may feature an adhesive recess configured for receiving an adhesive pad and/or provides for applying an adhesives therein so as to allow for securely affixing the device onto a user's body over a portion overlying the bladder.

In some embodiments the device housing may be utilized with and/or incorporated into a garment for example including but not limited to a diaper, underwear, belt, shirt, pants, skirt, the like or any combination thereof, wherein the garment facilitates placement of the device in a location overlying the bladder.

In some embodiments for example when utilizing the device with a garment such as a belt, the belt may provide an indication of the waist and/or girth of a user so as to determine the best transmitter frequency, up to 20 kHz, to utilize so to ensure measurement as the transmitter frequency is size dependent, wherein the higher frequency range, about 20 kHz, is utilized for small size users while smaller frequency, of about 5 kHz, is utilized for large size users, and for example very obese individuals may utilized a transmitter frequency of about 3 kHz.

In some embodiments the device may be provided in an optional form selected from a disposable device, single use device, a multi-use device, a combination thereof or the like.

In some embodiments the device may further comprise electronic circuitry comprising at least one or more selected from the group consisting of:

communication module, memory module, controller module, and real time clock, the like or any combination thereof.

In some embodiments controller module provides for processing and controlling the device functions as is known in the art.

In some embodiments memory module provides for storing data and facilitating operation of the device. Optionally memory module may be provided in any memory form as is known in the art.

In some embodiments the communication module may facilitate communicating data to and/or from the device. Optionally communication module may be provided with wired and/or wireless communication utilizing wireless and/or wired communication protocols as is known in the art for example including but not limited to WiFi, Bluetooth, near field, RF, IR, wired, cellular, wireless or the like.

Optionally the device may further comprise a sensor module that may comprise at least one or more sensor for example including but not limited to an Electromyography (EMG) sensor (EMG electrodes), pressure sensor, abdominal pressure sensor, temperature sensor, the like or any combination thereof.

In embodiments the device may be configured to determine the urinary bladder volume at a frequency from about 1 kHz up to about 20 kHz. Optionally determining the urinary bladder volume may be performed at a frequency of up to about 20 kHz. Optionally determining the urinary bladder volume may be performed at a frequency from about 5 kHz.

In some embodiments of the present invention provide a system for determining and/or assessing the level of fullness of the urinary bladder. The system comprising an external transmitter and/or emitter device for generating a sound wave, an internal and/or implanted device configured for receiving the transmitted sound, and at least one processing device that is in communication with the internal device and the external device.

In some embodiments of the present invention provide a system for determining and/or assessing the level of fullness of the urinary bladder wherein the system comprises an internally placed and/or implanted device, within the urinary bladder, the internal device having a transmitter and/or emitter device for generating a sound wave, an external device configured for receiving the internally transmitted sound, and at least one processing device that is in communication with the internal device and the external devices.

Optionally the internal device may be an implantable device that is preferably placed within the lumen of the urinary bladder. Optionally the internal device may be placed along a surface of the urinary bladder.

In embodiments the device and/or system according to embodiments of the present invention may provide for determining the bladder volume. Optionally the device and/or system according to embodiments of the present invention may provide an approximation of the level of urinary bladder fullness, therein providing an estimated level of fullness on a course percentage scale in the order of 0-100% with 10% graduations.

In some embodiments the device and/or system may utilize and/or comprise an external processing device that may be provided in the form of an external processing unit for example including but not limited to a mobile communication and processing device, smartphone, computer, server, call center, health care provided server, dedicated processing and communication device, mobile telephone, PDA, or the like device preferably comprising display, communication and processing capabilities.

In some embodiments, the system may further comprise and/or utilize optional auxiliary devices to facilitate performing urodynamic analysis. Optionally auxiliary device may for example include but is not limited to urinary absorbent pads, external catheters, urinary collection bags, stimulating electrodes, surface electrodes, implantable urinary incontinence devices, incontinence cuff and pump or the like.

In some embodiments of the present invention provides a method for determining a plurality of urodynamic parameter and performing urodynamic analysis based on data provided from the device according to the present invention, most preferably comprising the volume of the urinary bladder. Most preferably the method according to the present invention provides urodynamic analysis in a non-clinical setting.

Unless otherwise defined the various embodiment of the present invention may be provided to an end user in a plurality of formats, platforms, and may be outputted to at least one of a computer readable memory, a computer display device, a printout, a computer on a network or a user.

Unless otherwise defined, all technical and scientific terms used herein have the same meaning as commonly understood by one of ordinary skill in the art to which this invention belongs. The materials, methods, and examples provided herein are illustrative only and not intended to be limiting. Implementation of the method and system of the present invention involves performing or completing certain selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 4A-B are schematic illustrations, showing use of the device according to an embodiment of the present invention;

FIG. 6A-B show a schematic illustration showing use of an embodiment the device under different conditions according to an embodiment of the present invention;

FIG. 7A-B show a graphical depiction of the measurement provided by the device according to an embodiment of the present invention; \

FIG. 9A-D show a schematic graphical depiction of the analysis provided with device and system according to embodiments of the present invention.

DESCRIPTION OF THE PREFERRED EMBODIMENTS

The principles and operation of the present invention may be better understood with reference to the drawings and the accompanying description. The following figure reference labels are used throughout the description to refer to similarly functioning components are used throughout the specification hereinbelow.

Figure 1:
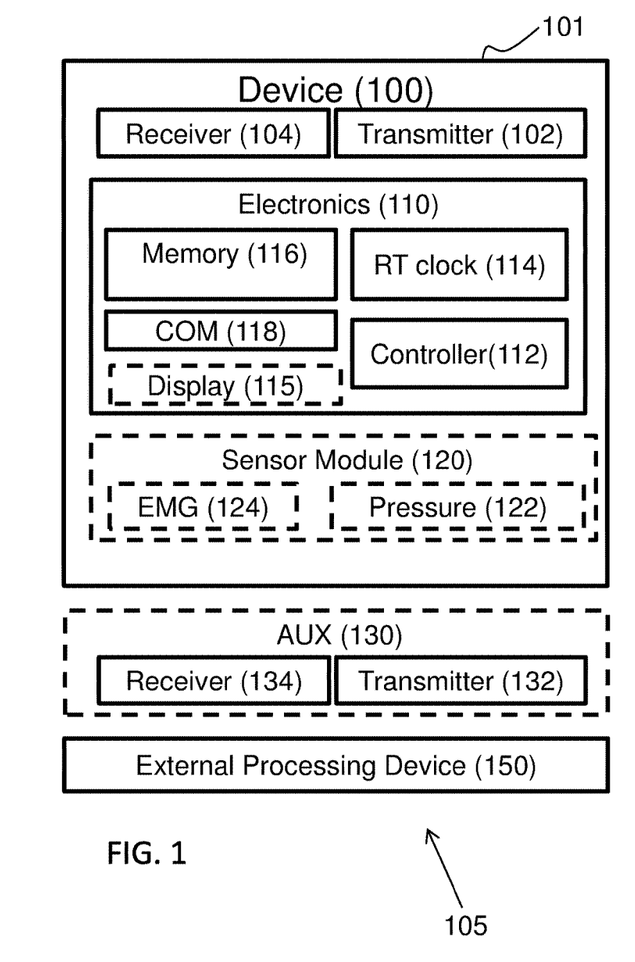
FIG. 1 is a schematic block diagram of an exemplary device according to an optional embodiment of the present invention.

60 urinary bladder;
55 user's body;
100 Urodynamic device;
105 system;
101 device housing;
101s adhesive recess;
102 acoustic transmitter;
102s acoustic signal;
104 acoustic receiver;
104s receiver signal;
104a low volume signal;
104b large volume signal;
106 vertical distance;
108 positioning module;
110 electronic circuitry module;
112 controller module;
114 real-time clock;
116 memory module;
118 communication module;
120 sensor module;
122 pressure sensor;
124 EMG sensor;
130 auxiliary device/internal bladder device;
132 aux sound transmitter;
134 aux sound receiver;
150 external processing unit/device;

FIG. 1 provides a schematic block diagram of device 100 according to an embodiment of the present invention, device 100 utilized for determining a user's urinary bladder volume. Most preferably the bladder volume may be utilized to provide a urinalysis, and/or uroflowmetry study and/or to treat or facilitate treatment of individuals experiencing incontinence and/or bed wetting in children. Device 100 determined urinary bladder volume by propagating an acoustic signal of up to 20 kHz toward the bladder and processing the reflected acoustic signal to determine the bladder volume. In embodiments the reflected acoustic signal is processed by comparatively assessing the amplitude of the resonance reflected acoustic signal.

In embodiments device 100 may be utilized to determine uroflowmetry analysis for example including but not limited to bladder filling rate, bladder emptying rate, incomplete voiding, the like or any combination thereof.

Device 100 comprises a housing 101, a sound wave generating transmitter 102, a sound wave receiver 104, and an electronic circuitry module 110.

Optionally device 100 may further comprise a sensor module 120.

Optionally and preferably electronic circuitry module 110 may comprise at least one or more sub-modules selected from the group consisting of: communication module 118, memory module 116, controller module 112, and real time clock 114, the like or any combination thereof. Optionally circuitry module 110 may further comprise a display module 115, for displaying and/or visually interfacing with a user.

Optionally controller module 112 provides for processing and controlling the overall device functions as is known in the art. Optionally and preferably controller module may be provided with a controlling means selected from a switch and/or button that is configured to further provide for controlling the functionality of device 100. Controller module 112 may further comprise a learning module provided for learning an individual user so as to ascertain the individuals bladder volume based on use of the device.

Optionally memory module 116 provides for storing data and facilitating operation of the device. Optionally memory module 116 may be provided in any memory form as is known in the art.

Real time clock (RT) 114 to facilitate accurate timing measurement of device 100.

Optionally the communication module 118 may facilitate communicating data to and/or from device 100. Optionally communication module 118 may be provided with wired and/or wireless communication capabilities utilizing wireless communication and/or wired communication protocols as is known in the art for example including but not limited to WiFi, Bluetooth, Near Field Communication (NFC), radio frequency (RF), infrared (IR), optical communication, acoustic communication wired, the like, or any combination thereof.

Optionally communication module 118 may be provided for communication with at least one or more processing and communication device 150 for example including but not limited to a computer, mobile telephone, smartphone, mobile communication device, cloud based processing device, server, network computer or the like communication and processing device, an any combination thereof. Optionally such an external processing device 150 may be utilized to communicate with and/or control the activity of device 100 by way of communicating a control signal to activate and/or deactivate device 100. Optionally communication module 118 and processing device 150, for example in the form of a mobile communication device, may be utilized to communicate results to a user so as to allow a user to visualize bladder volume levels. Processing device 150 may be configured to perform data processing of data obtained with device 100 so as to determined bladder volume. Accordingly device 150 may be utilized to provide/communicated data to device 100 so as to be processed by device 100. Optionally device 150 may be utilized to receive data measured with device 100 and/or additional devices so as to be processed to facilitate bladder volume determination and/or uroflowmetry analysis.

Figure 4A:
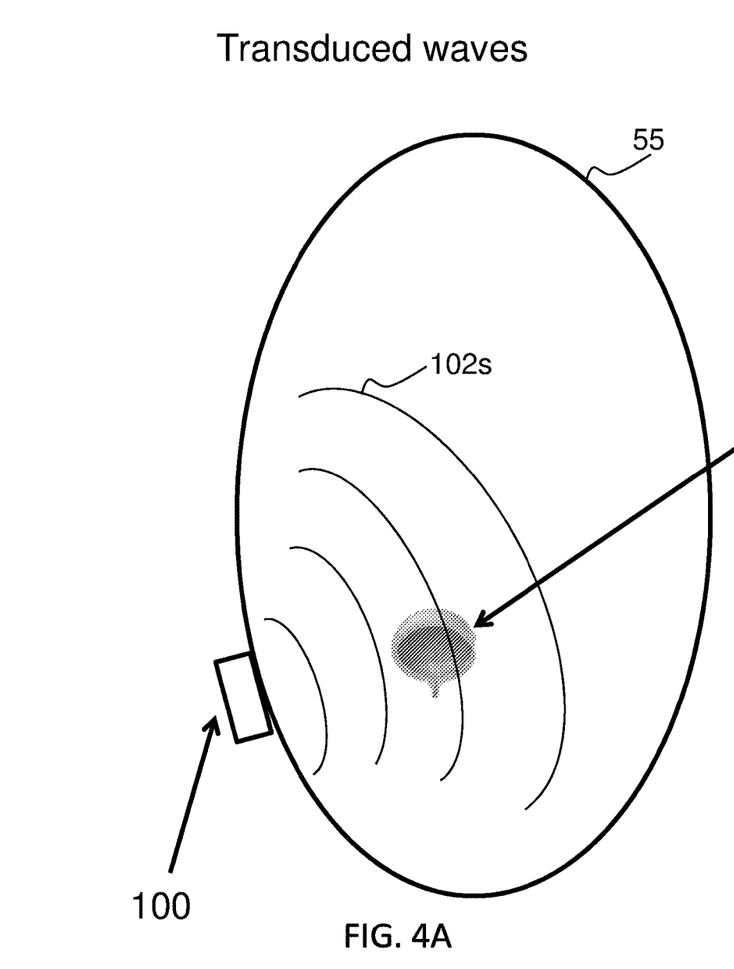
Figure 4B:
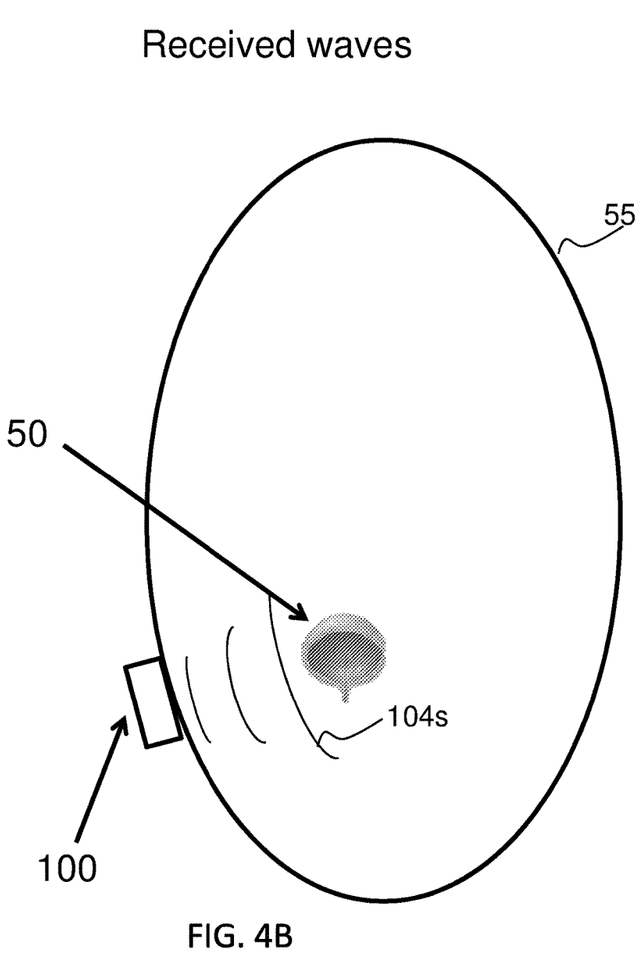

Device 100 provides for assessing the level of urinary bladder fullness and/or volume by analyzing and/or processing soundwaves having a frequency of up to about 20 kHz. FIG. 4 shows how device 100 may be used to determine bladder volume. Most preferably the sound wave analysis and/or processing includes: emitting a sound wave 102s with transmitter 102 in the selected frequency range of up to 20 kHz toward the urinary bladder 50, FIG. 4A, and thereafter detecting the reflected and/or refracted soundwaves signal 104s returning from the urinary bladder surface, FIG. 4B, with receiver 104. The return sound wave signal 104s is analyzed and/or processed with at least one of internal processor 112 and/or external processor 150 in order to determine and/or indicative the level of fullness of the urinary bladder, as discussed and shown in FIG. 7-9.

Preferably the sound wave is generated with transmitter 102 and the return signal is sensed by receiver 104. Preferably transmitter 102 and receiver 104 are sensitive to the sound signal frequency preferably up to about 20 kHz Optionally transmitter 102 may be provided in the form of a speaker and receiver 104 in the form of a microphone.

Preferably transmitter 102 is provided in the form of a piezoelectric device for generating resonating percussion and/or sound of up to 20 kHz and more preferably between about 1 kHz and up to about 20 kHz.

In embodiments transmitter 102 may be provided from a piezoelectric device comprising at least one or more piezoelectric elements capable of transmitting an acoustic signal of up to about 20 kHz. In embodiments transmitter 102 may be provided from a plurality of piezoelectric elements each generating a signal having different frequency within the range of about 1 kHz and up to about 20 kHz. For example transmitter 102 may comprise an array of piezoelectric elements each configured to transmit an acoustic signal for example including 1 kHz, 5 kHz, 10 kHz, 15 kHz, and 20 kHz. For example transmitter 102 may comprise an array of piezoelectric elements each configured to transmit a different acoustic signal for example including 1 kHz, 3 kHz, 5 kHz, 10 kHz, 12 kHz, 15 kHz, and 20 kHz.

In embodiments device 100 may be fit with one transmitter 102 having multiple frequency bands of up to 20 kHz wherein the sound frequency selected is based on the size and/or age of the user. For example, a child or similarly small individual may utilize a transmitter having a higher frequency from 5 kHz and up to about up to 20 kHz, while an adult or large size user would utilize a transmitter having a frequency that is up to about 5 kHz more preferably from about 1 kHz up to about 5 kHz.

Preferably control of transmitter 102 and receiver 104 is provided with electronics module 110 comprising controller 112 for generating and processing data.

Figures 2A, 2B:
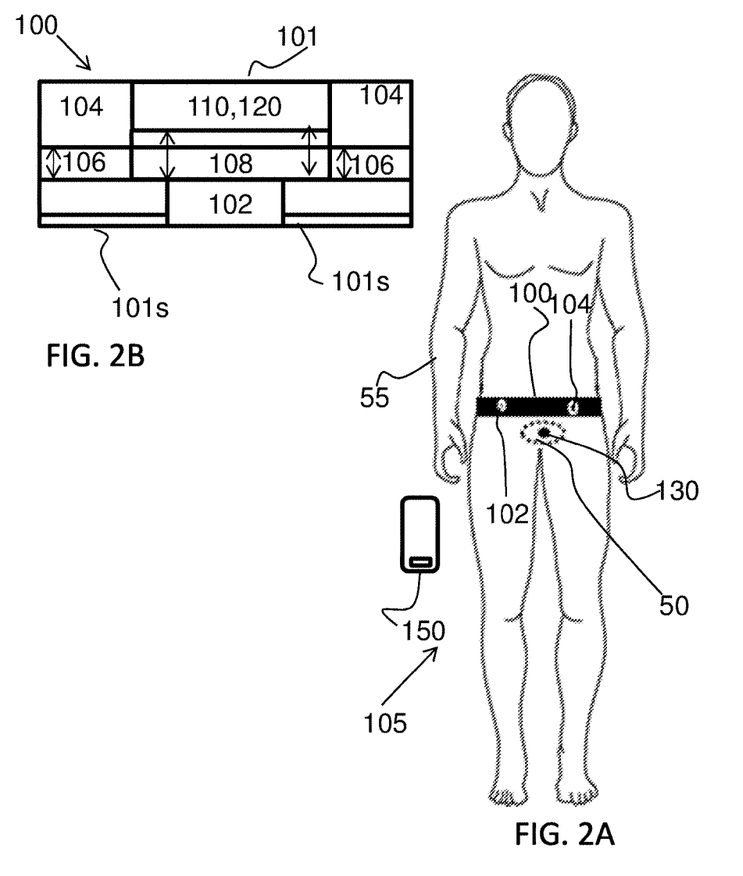
FIG. 2 is a schematic illustration, showing an optional placement of an exemplary device and system according to an optional embodiment of the present invention.
Figure 5:
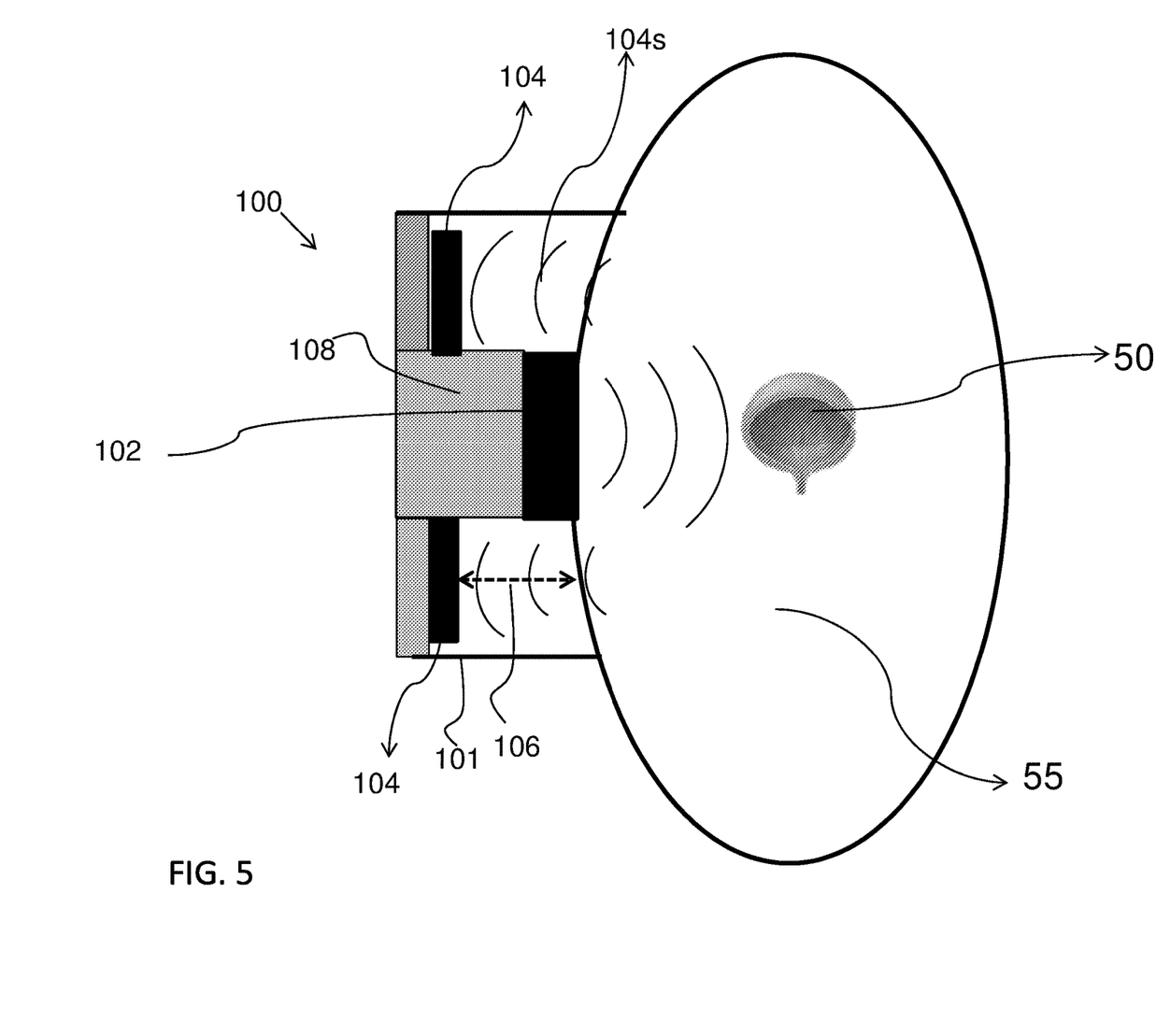
FIG. 5 is a schematic illustration showing an optional embodiment the device according to an optional embodiment of the present invention.

In some embodiments transmitter 102 and receiver 104 are arranged within housing 101 such that they are separated by a vertical distance 106 from one another, for example as shown in FIG. 2B and FIG. 5. More preferably transmitter 102 is placed adjacent to the user's body such that the transmitter 102 is coupled and/or affixed to the user's skin overlying the bladder 50, FIG. 5, while receiver 104 is placed at vertical distance 106 from transmitter 102 such that there is space there between.

In some embodiments the vertical space 106 is controllable and may be from about 0.1 mm and up to about 20 mm. In some embodiments the receiver 104 is placed up to about 10 mm above transmitter 102. Vertical distance 106 preferably improves the signal to noise ratio so as to improve the signal received at receiver 104 so as to ensure that the receiver is not coupled to the abdominal surface of user 55.

In embodiments the space 106 between transmitter 102 and receiver 104 may be filled with a flowing fluid for example including but not limited to a gas, air, liquid, water, gel, oil, viscous liquid, plasma, or the like medium that is conducive for transmitting and/or propagating the acoustic signal 104s reflected by the bladder.

In some embodiments the vertical space 106 may be controlled by utilizing a mechanical spacer of variable size.

In some embodiments the vertical space 106 may be controlled by utilizing a positioning module 108 to control the vertical distance 106 between receiver 104 and transmitter 102, as will be discussed with respect to FIG. 2B and FIG. 5.

In embodiments the sound wave received from the urinary bladder is processed and/or analyzed with a controller/processor 112 of electronics module 110. In some embodiments processing may be provided by an external and/or auxiliary processing device 150 for example including but not limited to a smartphone, mobile phones, or the like mobile processing and communication device that is in communication with device 100.

In some embodiments data and/or signal processing may be internal to the device. In some embodiments data and/or signal processing may be provided by an external and/or auxiliary and/or remote processing device 150, for example including but not limited to a computer, mobile communication device, cloud based processing device, server, network computer or the like communication and processing device, and any combination thereof. Most preferably device 100 is placed externally along the user's 55 abdominal anatomy overlying the urinary bladder 50, FIG. 2A, so as to place the device in proximity to the urinary bladder to facilitate volume measurement, soundwave transmission and receiving (pickup).

In embodiments housing 101 may feature a biocompatible adhesive 10i s, FIG. 2B, for example in the form of a pad and/or or the like sticker that is utilized to secure device 100 directly onto a user's 55 skin, for example along a portion of the abdomen overlying the urinary bladder 50, for example as shown in FIG. 2A. In embodiments housing 101 may feature a recess, FIG. 2B, provided for receiving a biocompatible pad and/or sticker and/or the like biocompatible adhesive so as to approximate device 100 to a user as previously described.

In some embodiments device 100 may be placed in a housing 101 that is configured to be attached to a fixing means, for example in the form of a belt, so as to allow for placement externally over the urinary bladder for example in the form of a belt.

In some embodiments device housing 101 may be incorporated and/or provided in the form of a garment for example including but not limited to a diaper, underwear, belt, shirt, skirt, pant the like or any combination thereof to facilitate device 100 placement over the urinary bladder 50, wherein the garment facilitates placement of the device in a location overlying the bladder.

In some embodiments for example when utilizing the device with a garment such as a belt, the belt may further provide an indication of the waist and/or girth of a user so as to determine the best transmitter frequency, up to 20 kHz, to utilize so to ensure measurement as the transmitter frequency is size dependent, wherein the higher frequency range, about 20 kHz, is utilized for small size users while smaller frequency, of about 5 kHz, is utilized for large size users, and for example very obese individuals may utilized a transmitter frequency of about 3 kHz.

Optionally device 100 or portions thereof may be provided in optional forms selected from a disposable device, single use device, a multi-use device, a combination thereof or the like.

Device 100 may optionally comprise a sensor module 120 comprising at least one or more sensors for example including but not limited to an Electromyography (EMG) sensor 124, a pressure sensor 122, abdominal pressure sensor, temperature sensor, galvanic skin conductance sensor, the like or any combination thereof.

FIG. 1 further shows device 100 that may be further utilize to form a system 105 that is provided for assessing urinary bladder volume by pinging bladder 50 with a sound signal having a frequency of up to about 20 kHz, and optionally from about 1 kHz up to about 20 kHz.

System 105 comprises device 100 and an external processing and communication device 150 as previously described.

In an optional embodiment of system 105 may further comprise an auxiliary device 130 provided in the form of an implanted urinary bladder device comprising at least one and/or both of a receiver 132 and transmitter 134. Optionally auxiliary device 130 may be provided in the form of an implantable device that is functionally coupled with device 100 so as to facilitate bladder volume measurements. For example a device 100 may be used to generate a sound signal with transmitter 102 that is picked up by aux receiver 134 and/or vice versa where a sound signal is transmitted with aux transmitter 132 to be picked up by device receiver 104, to provide for determining bladder volume. Auxiliary device 130 comprises the necessary electronics to render it functional independent of device 100 therein comprising power, communication and processing capabilities.

In some embodiments device 100 and auxiliary device 130 may be utilized simultaneously to ping a sound wave having a frequency of up to about 20 kHz, optionally form about 1 kHz up to about 20 kHz, to determine bladder volume in two parallel measurements that are averaged and/or weighted to determine a combined bladder volume based on both measurements.

In embodiments system 105 may comprising device 100, auxiliary device 130 and external processing device that provides for mediating and/or interfacing communication between device 100 and auxiliary device 130.

In some embodiments device 100 and auxiliary device 130 may be in direct communication with one another.

FIG. 2A-B shows a schematic illustrative diagram of device 100 and system 105 according to embodiments of the present invention.

FIG. 2A shows device 100 having a housing 101 in the form of a belt that is fit onto a user 55 and placed along the abdomen overlying the bladder 50. As shown in FIG. 2A bladder 50 is further fit with an optional auxiliary implanted device 130, as previously described.

FIG. 2B shows device 100 having housing 101 that features an adhesive pad 101s provided to fit with a biocompatible adhesive and/or sticker so as to allow to affix and/or securely couple device 100 to user 55 along the user's abdominal surface overlying bladder 50, also depicted in FIG. 5.

Preferably a resonating sound wave having a frequency of up to about 20 kHz is generated by device 100 from emitter 102. As shown in FIG. 4A-B, the acoustic signal 102s is configured to propagate from emitter 102 toward bladder 50 causing the signal to reflect of the bladder forming a return acoustic signal 104s. The return sound signal 104s from the bladder 50 is sensed with received 104 disposed about device 100 where the return signal 104s is processed to determine the volume of bladder 50.

In some embodiments device 100 may be used in conjunction with an auxiliary device 130 and/or external processor 150 to determine the volume of bladder 50, as previously described.

In some embodiments device 100 is in continuous communication with mobile communication device 150 via device 100 via communication module 118, not shown. Optionally operations of device 100 may be controlled remotely with device 150.

In some embodiments the volume of bladder 50 determined with device 100 and/or system 105 may be communicated and displayed on device 150. In some embodiments system 105 may further comprise and/or utilize additional optional auxiliary devices to facilitate performing urodynamic and/or uroflowmetry analysis. Such additional auxiliary device that may be utilized may for example include but is not limited to urinary absorbent pads, external catheters, urinary collection bags, stimulating electrodes, surface electrodes, implantable urinary incontinence devices, incontinence cuff and pump or the like.

FIG. 2B shows a schematic box diagram of an optional device 100 and FIG. 5 shows device 100 fit with a user 55 over bladder 50. The schematic illustration of device 100 shows transmitter 102 and receiver 104 are separated by a vertical distance 106 and wherein a spacer and/or positioning module 108 may be utilized to control the vertical distance 106 employed. In some embodiments positioning module 108 may be realized as an actuator and/or the like motor for example a piezoelectric actuator. In some embodiment positioning module 108 may be realized in the form of a mechanical spacer that may be utilized to control the distance 106 between transmitter 102 and receiver 104.

Figure 3:
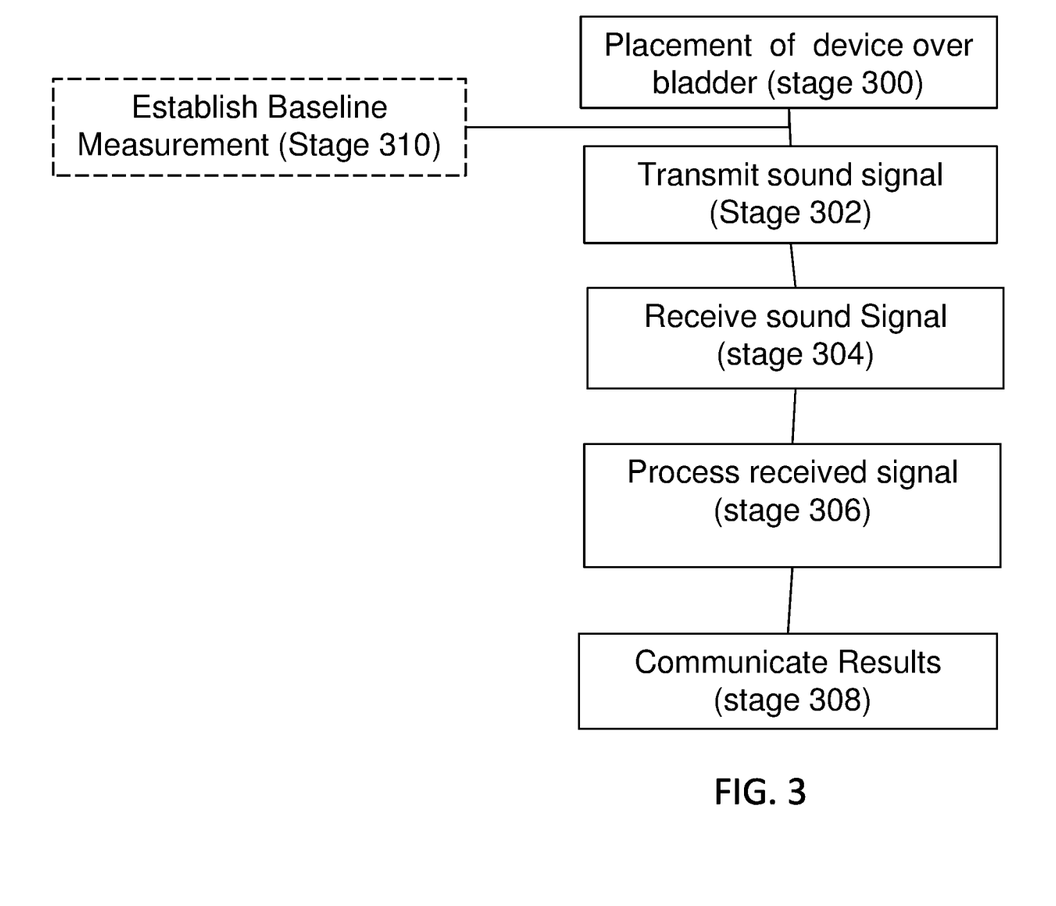
FIG. 3 is a flowchart depicting a method for determining urodynamic parameters according to an optional embodiment of the present invention.

FIG. 3 shows a flowchart depicting an optional method of use of device 100 provided alone or as part of system 105, for determined bladder volume.

First in stage 300, urodynamic device 100 is coupled to a user 55 placed along the abdominal surface so as to overly the urinary bladder 50. Preferably device 100 is coupled and/or affixed to user 55 with biocompatible adhesive 101s.

In some embodiments, proper placement of device 100 may be determined device housing 101 that may be provided in optional forms, for example including but not limited to a belt, pant, shirt, skirt, undergarment, underwear or the like.

In some embodiments, the abdominal surface overlying transmitter 102 may first be applied with a water based gel, medical gels or the like gels, for example including but not limited to ultrasound gels for facilitating sound propagation and conduction from device 100 and in particular transmitter 102 and the skin of user 55.

Next in stage 302, transmitter 102 of device 100 generates an acoustic resonance signal 102s having a frequency of up to about 20 kHz, more preferably the transmitter generates a resonant frequency that is based on the size (girth) of user 55, wherein for larger users, based on girth and/or waist size, and/or BMI measurements, a frequency of up to about 5 kHz is utilized while for smaller users a resonant frequency of up to about 20 kHz is utilized, and propagated and/or transmitted toward bladder 50.

Next in stage 304, the transmitted signal 102s is allowed to propagate toward the bladder 50 producing a reflected and/or refracted signal 104s that is received by receiver 104, for example as shown in FIG. 4A-B. As will be discussed in greater detail with respect to FIG. 6-9 the refracted signal 104s varies with the volume of bladder 50 therein allowing device 100 and/or system 105 to determine the bladder volume, therein device 100 provides an acoustic signature at different bladder volumes.

In some embodiments the transmitted signal 102s may be picked up by an optional implanted auxiliary device 130, for example with receiver 134, which is thereafter retransmitted by device 130 toward receiver 104 and/or communicated to processing device 150 for determining the volume of bladder 50.

In some embodiments an auxiliary device 130 may be utilized to generate a resonant acoustic signal with transmitter 132 the signal having a frequency of up to 20 kHz and more preferably from 1 kHz and up to about 20 kHz, while receiver 104 of device 100 is configured to receive an analyze the signal to determine bladder volume.

Next in stage 306, the received sound wave 104s is analyzed and/or processed preferably with at least one of processor module 112 and/or external processing device 150 to determine bladder volume. Optionally bladder volume is determined by way of comparison to a baseline measurement provided under controlled conditions, in an optional preliminary stage 310 as will be discussed below.

Next in stage 308, the bladder volume is communicated to a user and/or a third party either via an optional display 115 of device 100 and/or external device 150.

In some embodiments bladder volume results may be communicated to an external processing device 150 for further analysis for example for performing a urinalysis, uroflowmetry analysis, incontinence treatment, urodynamic analysis or the like.

In some embodiments the bladder volume may be utilized to assist individuals suffering from incontinence is to provide them with an indicator of the level of fullness of the urinary bladder so as to facilitate control. Preferably such an indication may be provided directly to the subject and/or to a caregiver so as to allow a user to gain control over the bladder of a subject suffering from incontinence. Similarly such information may be used to facilitate teaching children and/or the elderly to gain and/or re-gain control of the bladder.

Optionally the system may further comprise and utilize optional auxiliary devices to facilitate performing urodynamic analysis. Optionally auxiliary device may for example include but is not limited to urinary absorbent pads, external catheters, urinary collection bags, stimulating electrodes, surface electrodes, implantable urinary incontinence devices, incontinence cuff and pump or the like.

In an optional preliminary stage 310, as depicted by dashed lines, a baseline measurement is established under controlled conditions. A learning phase may be required implemented to provide and establish a baseline measurement for a user. More preferably such a baseline measurement may be utilized to determine future bladder volume measurement for a user 55. Most preferably the baseline measurement provides for determine how the bladder 50 of user 55 behaves acoustically when subjected to the transmitted signal acoustic signal 102s and the characteristics of the return signal 104s it generates under different predefined conditions, for example including but not limited to empty state, full state, intermediate states of variable volume, during active urinary filling, active urinary emptying, the like or any combination thereof. Preferably a baseline measure is established based on a measurements provided during an empty state and at least one or more liquid volume states of a predetermined liquid volume for example 150 cc, 200 cc, 250 cc or 500 cc, or the like.

Most preferably the baseline measurement with device 100 provide for establishing the acoustic signature for a user's bladder 50. The established baseline measurement allow device 100 to be utilized to determine instantaneous bladder volume in a noninvasive and/or passive manner by way of comparison to the baseline measurements.

FIG. 4A-B provide a schematic depiction of the concept of the use of device 100 with a user 55 so as to determine the volume of bladder 55. FIG. 4A shows the transmission of an acoustic resonance signal 102s having a resonance frequency of up to about 20 kHz, that is transmitted by device 100 preferably with transmitter 102 and directed toward bladder 50. FIG. 4B shows the reflected and/or refracted waves 104s resultant from the interaction between bladder 50 and transmission 102s. Signal 104s is received by device 100 with receiver 104 and analyzed utilizing processing module 112, the processing will be discussed in greater detail in FIG. 7-9.

FIG. 5 provides a further schematic depiction of device 100 showing its use in a similar fashion to that provided by FIG. 4A-B. However, FIG. 5 shows device 100 wherein receiver 104 and transmitter 102 are disposed in a housing 101 having a vertical space 106 there between, and wherein the dimension of the space 106 that is utilized is controlled with positioning module 108.

Accordingly the distance 106 may be filled with a flowing fluid for example air, that is used as a resonating space for return signal 104s. The return signal is then received by receiver 104 to determine the bladder volume. Vertical distance 106 is preferably in the range of 0.1 mm up to about 20 mm.

In some embodiments vertical distance 106 may be controllable. Preferably the position of receiver 104 is adjusted relative to the fixed position of transducer 102. Optionally the vertical adjustment of distance 106 is provided by a positioning module 108 that is controlled with and functionally associated with electronics module 110. For example positioning module 108 may be provided in the form of a stage including and/or associated with at least one or more receivers 104. Preferably the vertical position of the stage may be adjusted so as to control distance 106 between transducer 102 and received 104. In some embodiments the positioning module 108 may be adjusted so as to improve signal to noise ratio (SNR).

In some embodiment positioning module 108 may be provided in the form of a mechanically adjustable spacer that is adjusted as needed.

Optionally distance 106 is adjusted with module 108 based on at least one or more parameters for example including but not limited to user's size, user's BMI, resonant frequency of transmitter 102, signal strength, the like or any combination thereof.

Figure 6A:
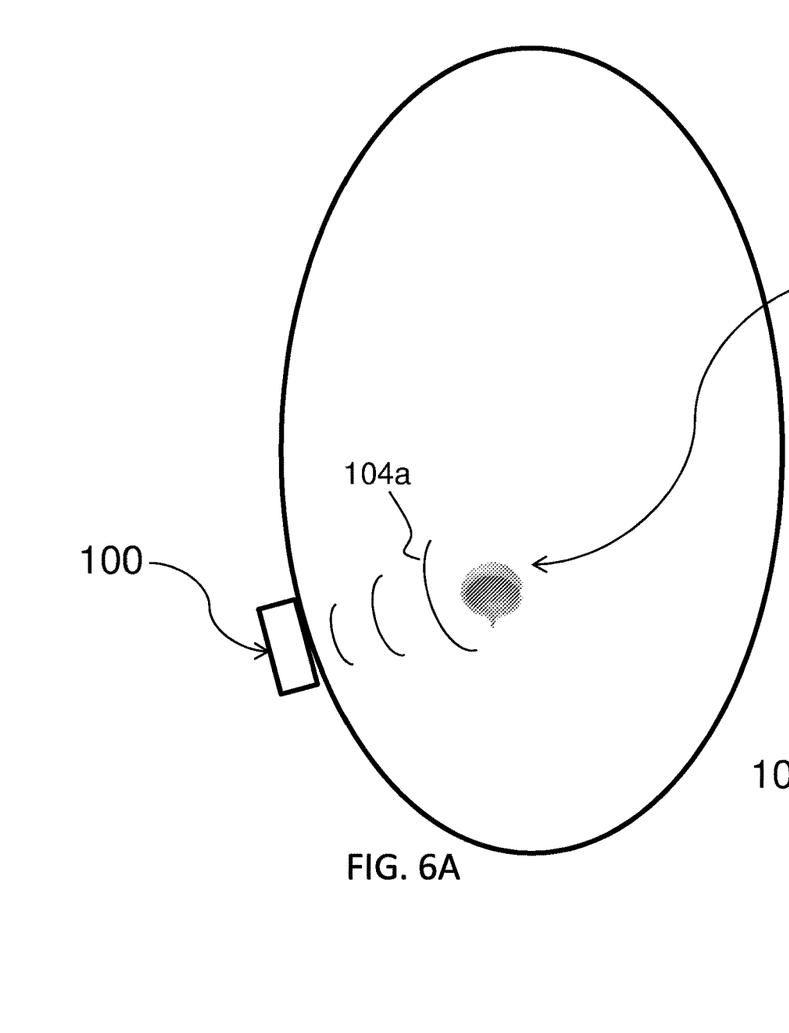
Figure 6B:
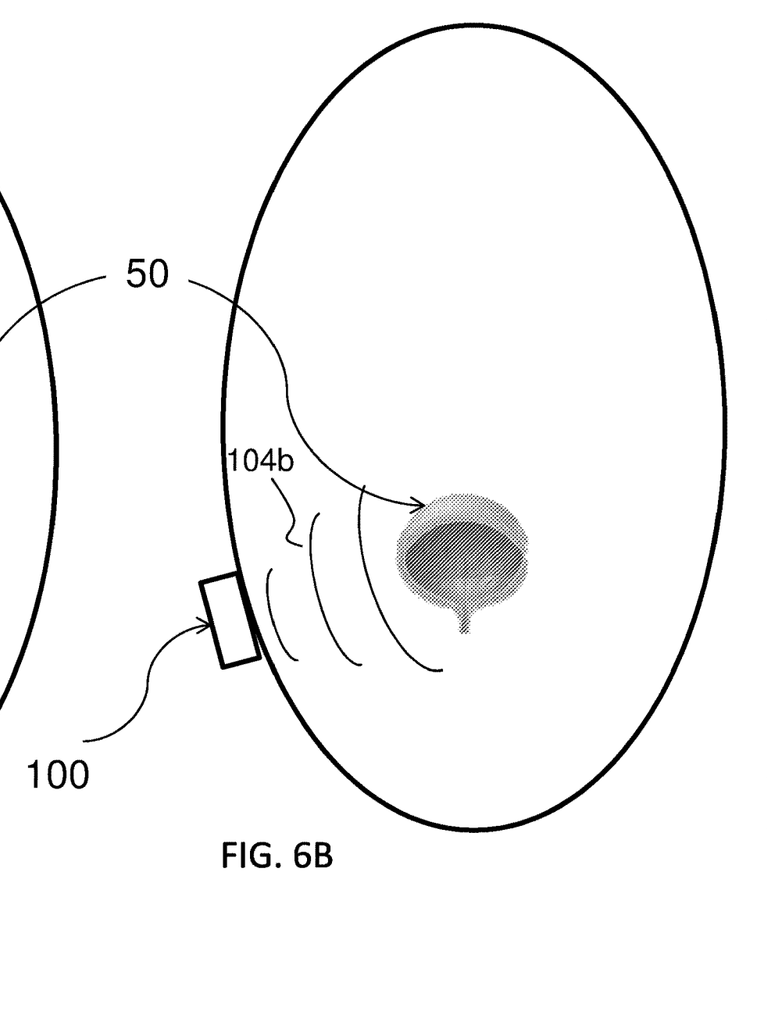

FIG. 6A-B provide a schematic depiction of use of device 100 wherein the reflected signal 104s provided by bladder 50 behaves differently under different bladder volume conditions. That is a low volume and/or empty bladder 50 as shown in FIG. 6A results in a transmitted signal 104a, having lower amplitude, shown in FIG. 8 solid line. A large volume and/or non-empty bladder 50 as schematically shown in FIG. 6B results in a transmitted signal 104b, having a larger amplitude also shown in FIG. 8 broken line (115 cc). Device 100 utilizes the amplitude of the echo signal 104s to determine the volume of bladder 50. Preferably a baseline measurement defining the behavior of a user's bladder 50 is provided so as to ascertain the baseline amplitude of an individual's echo signal 104s in response to a transmitted signal 102, under controlled conditions include an empty state and at least one predetermined volume defining a non-empty bladder state, for example having a predefined volume of 100 cc, 150 cc, 200 cc, 250 cc or the like.

EXAMPLES

Figure 7A:
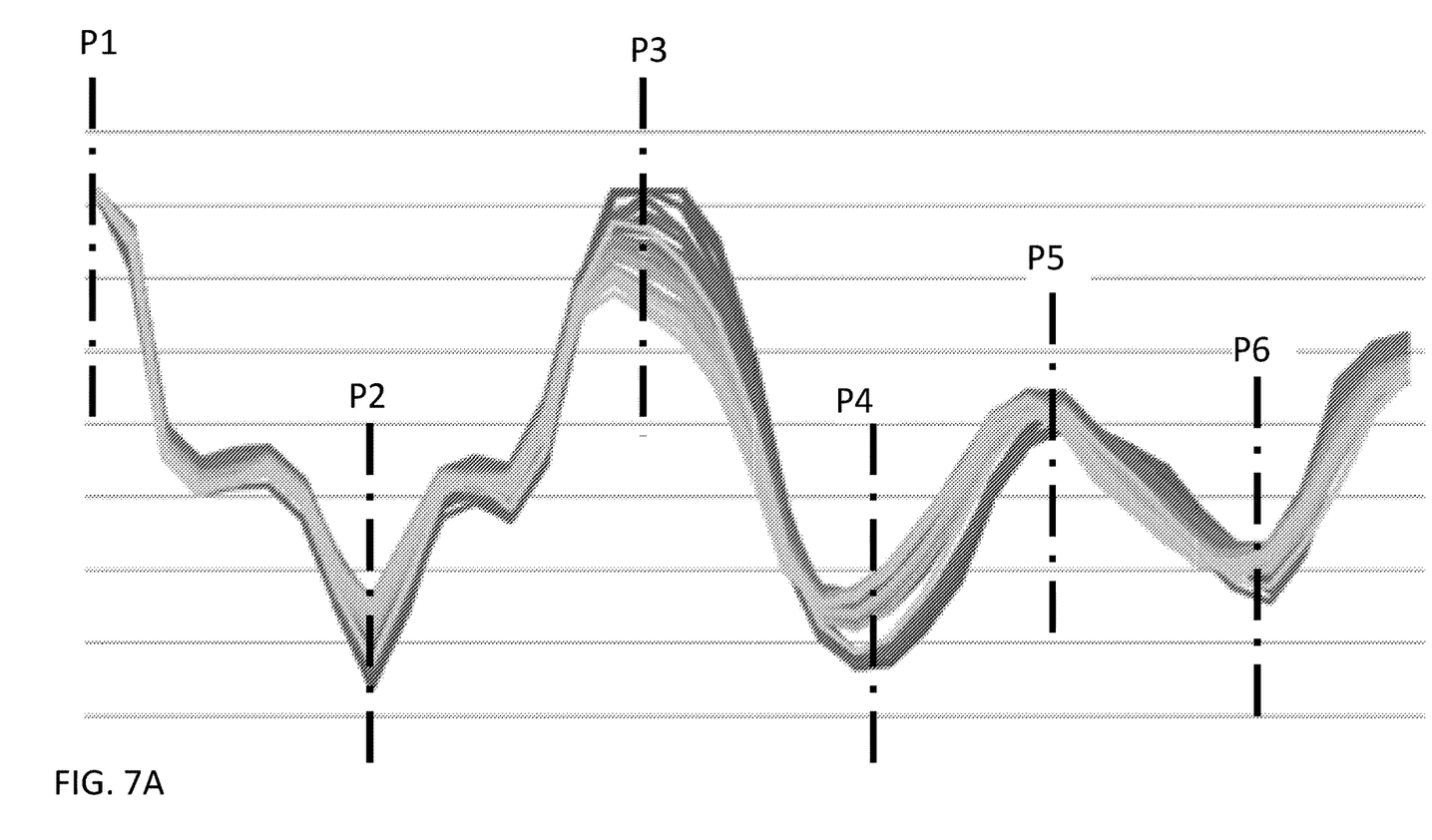
Figure 7B:
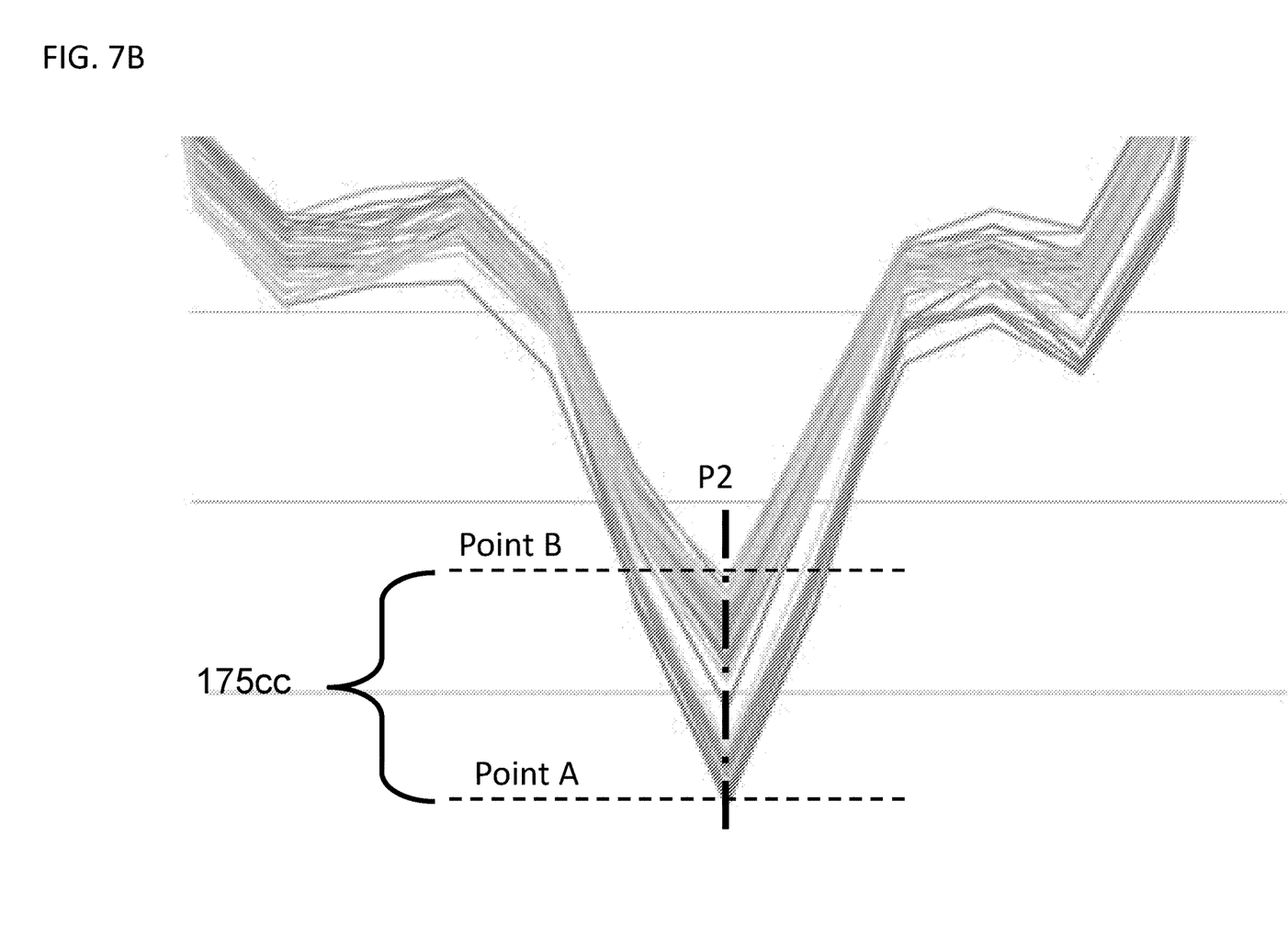

FIG. 7A-B show an example of echo measurements provided by device 100 according to the present invention over a period of 35 seconds during a bladder voiding experiment. The echo signal 104s received at receiver 104 of device 100 during a bladder voiding experiment. FIG. 7A shows raw data curve of the evolution of the echo signal 104s received with receiver 104 of device 100 utilizing a transmitter 102 having a piezoelectric resonating element having a 3 kHz resonant frequency. Each line represents an echo signal 104s at different iteration time during the bladder emptying measurement. As can be seen in a close up of the segment labelled P2 that is shown in FIG. 7B. Accordingly, the curve having the lowest amplitude marked 'Point A' represent the first echo iteration where the bladder is full, the curve having the highest amplitude in the segment represent the last echo iteration where the bladder is empty, marked 'Point B'. The difference between points A and B are show that the amplitude of the echo signal 104s produced by bladder 50 is different under different bladder volume conditions; namely, empty in Point B and filled or non-empty at point A, despite a constant transmitted resonant acoustic signal 102s having a frequency of 3 kHz provided by transmitter 102. In the results shown the difference amplitude between points A and B is proportional to 175 cc filled bladder at the onset of the bladdery emptying experiment and a 0 cc ('empty') state at the end. Most preferably such a bladder emptying experiment provides a baseline to allow device 100 to learn the behavior bladder 50 of user 55 with a 3 kHz transmitter 102, and receivers 104, that are disposed at a vertical distance 106 from transmitter 102. The baseline measurement under such controlled conditions will allow user 55 to use device 100 to determine bladder volume based on future return echo signals 104s under non-controlled conditions so as to determine instantaneous bladder volume.

Optionally such a baseline measurements may be provided during a bladder filling experiment where initially bladder is emptied, for example with a catheter, and allowed to be filled over time by a controlled and predefined volume. While as measurements are undertaken as the bladder is being filled.

Most preferably bladder volume is determined by recording the echo signal 104s as shown thereafter determine the peaks amplitude at different resonant frequency harmonics P1-P6. The peak amplitude data is thereafter utilized to determine the peak to peak difference between successive peaks of the same iteration, for example P1-P2, P2-P3, P3-P4 and P4-P5, for example as shown in FIG. 9A-D. In some embodiments peak to peak difference may be provided from non-successive peaks.

Most preferably the change in peak to peak amplitude between a full bladder and an empty bladder may reach aa level of up to about 3 dB.

Optionally during bladder emptying baseline measurements a reading at least 10 measurements per seconds and up to 1000 measurements a minute are generated.

Optionally during bladder inflow baseline measurements a reading is undertaken once every couple of minutes based on a normal bladder filling rate of 1 mL/minute, in embodiments during bladder filling measurements a burst of measurement may be undertaken every minute and more preferably about every 5 minutes.

Figure 8:
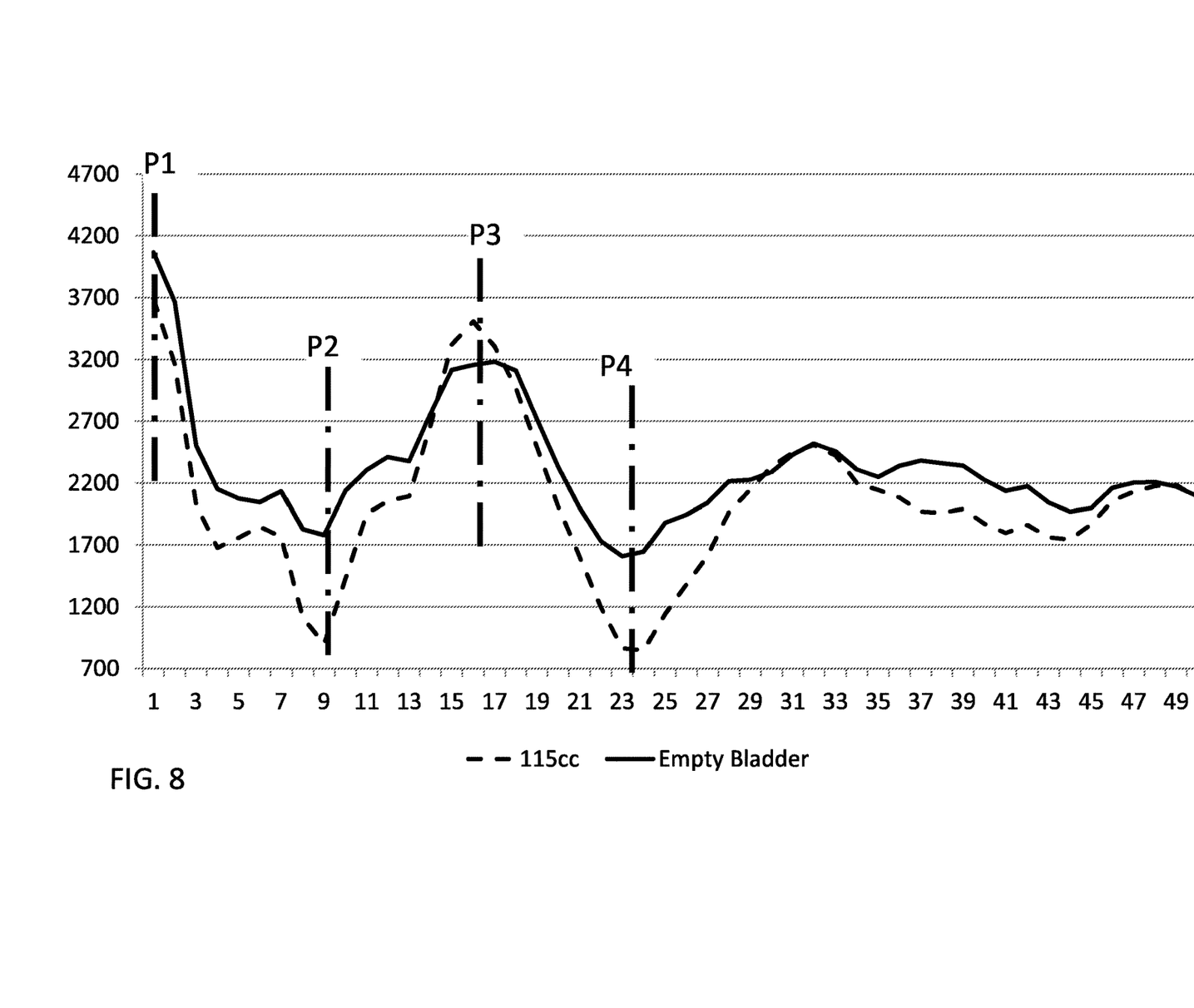
FIG. 8 shows a further graphical depiction of measurements provided by the device of the present invention under different conditions.

FIG. 8 shows an additional graphical depiction of the resonant echo signal 104s provided with device 100 showing the echo curve of an empty bladder, solid line, and the echo curve of a bladder having a bladder volume of 115 cc. FIG. 8 clearly shows the differences between curve amplitudes a peak locations P1-P4. The peak locations P1-P4 are utilized to correlate the volume to the curve amplitude at the peak locations. Accordingly, a resonant curve such as that shown in FIG. 8 shows the controllable conditions that allows for creation of a baseline for a given user. Such a baseline may be utilized to determine the instantaneous bladder volume by comparing an instantaneous reading to a baseline curve such as the depicted in FIG. 8.

Figure 9A:
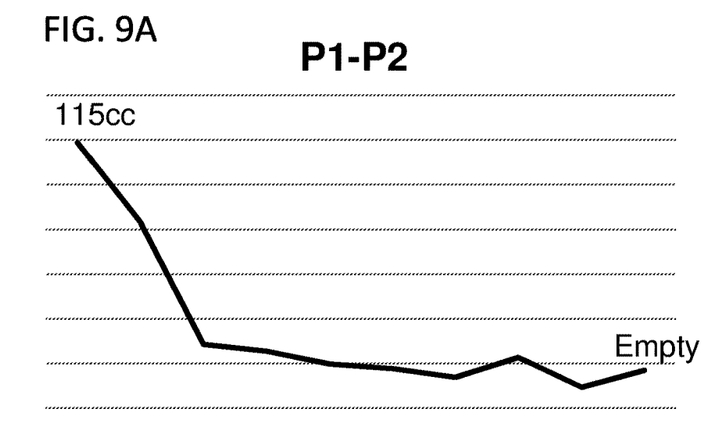

FIG. 9A-D show the peak to peak graphical calculation obtained from the data depicted in FIG. 8. FIG. 9A shows the peak to peak difference between P1-P2 difference curve where the peak amplitude at 115 cc is significantly different from the peak to peak amplitude when the bladder is empty.

Figure 9B:
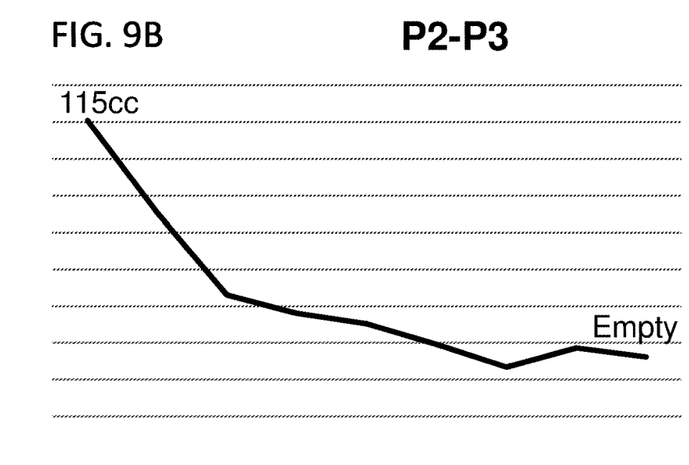

FIG. 9B shows the peak to peak difference between P2-P3.

Figure 9C:
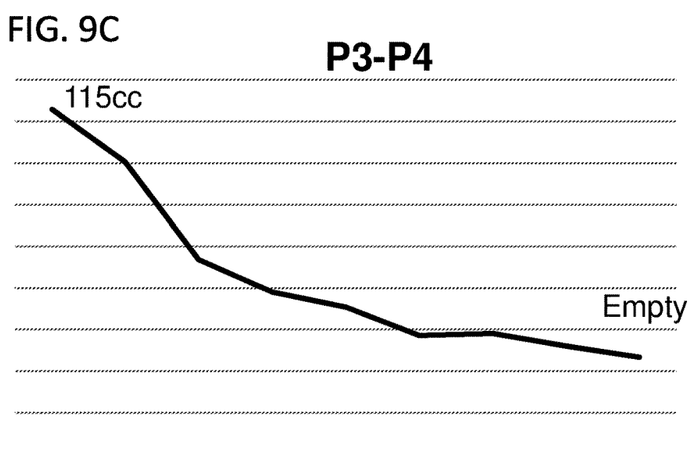

FIG. 9C shows the peak to peak difference between P3-P4.

Figure 9D:
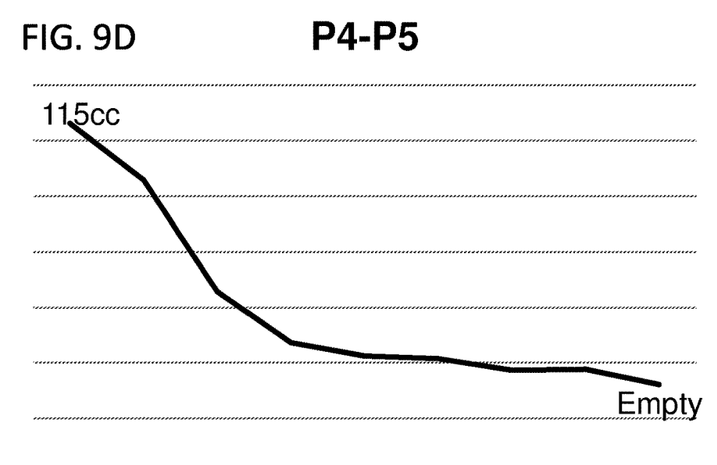

FIG. 9D shows the peak to peak difference between P4-P5.

As can be seen all of the graphs exhibit similar amplitude difference between successive peaks along the same curve, accounting for up to 3 dB amplitude difference in the signal that account for 115 cc bladder volume under controlled conditions.

Most preferably this analysis under control conditions provide for establishing a baseline which may be used to determine future instantaneous bladder volume when compared to the baseline reading.

While embodiments of the present invention have been described with respect to use for human subjects however this may be extended for use with pets or animals.

While the invention has been described with respect to a limited number of embodiment, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not described to limit the invention to the exact construction and operation shown and described and accordingly, all suitable modifications and equivalents may be resorted to, falling within the scope of the invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

Citation or identification of any reference in this application shall not be construed as an admission that such reference is available as prior art to the invention.

Section headings are used herein to ease understanding of the specification and should not be construed as necessarily limiting.

While the invention has been described with respect to a limited number of embodiments, it will be appreciated that many variations, modifications and other applications of the invention may be made.

What is claimed is:

1. A bladder volume detection device (100), the device comprising:
   a) a housing (101) configured for placement along an abdominal surface respective of the urinary bladder so as to allow for measuring the volume of the urinary bladder; said housing comprising an electronics module (110) including a processor (112), an acoustic transmitter (102) and at least one receiver (104), said housing characterized in that said acoustic transmitter (102) and said at least one receiver (104) are disposed therein in a manner wherein said transmitter (102) is disposed adjacent to an external surface of said housing and configured to be disposed proximal to or along the abdominal surface and wherein said at least one receiver (104) is disposed distally to said transmitter (102), and is forming an open space (106) between said transmitter (102) and said at least one receiver (104); wherein said receiver (104) is configured not to be directly coupled to the abdominal surface is configured to be at a distance at least equal to a vertical dimension of said open space; said device is further characterized in that said open space (106) has a vertical dimension of at least 0.1 mm and up to 20 mm;
   b) said transmitter (102) comprising a piezoelectric element configured to receive a pulse from said electronics module so as to generate a resonant frequency of up to 20 kHz utilized to ping the urinary bladder and wherein said at least one receiver (104) is configured to receive a return signal (104s) from the urinary bladder;
   c) said processor (112) configured to undertake processing of said return (104s) to determine the urinary bladder volume.

2. The device of claim 1 wherein said processor (112) is configured to determine the urinary bladder volume by generating an echo amplitude curve from each iteration of said echo signal (104s) and processing said signal (104s) curve to identify a peak to peak difference of successive peaks of the echo signal and wherein said peak to peak difference is compared to a normalized chart or a user specific normalized chart.

3. The device of claim 1 further comprising a positioning module (108) for controlling the vertical dimension of said open space (106).

4. The device of claim 3 wherein said positioning module (108) is adjusted based on at least one parameter selected from user's size, user's Body Mass Index (BMI), transmitter frequency, signal strength, any combination thereof.

5. The device of claim 1 wherein said transmitter (102) is configured to generate multiple pulse frequency bands of up to 20 kHz and wherein the frequency utilized is selected based on the waist size and/or girth of a user.

6. The device of claim 5 further comprising a sizing garment, said garment providing an indication of the waist and/or girth of the user so as to determine frequency band generated by said transmitter.

7. The device of claim 6 wherein said transmitter frequency is 3 kHz.

8. The device of claim 1 wherein said transmitter frequency is at least 5 kHz.

9. The device of claim 6 wherein said garment is selected from diaper, underwear, belt, shirt, skirt, pant or any combination thereof.

10. The device of claim 1 wherein said transmitter is a piezoelectric element having a resonant frequency of up to 5 kHz.

11. The device of claim 1 wherein said transmitter comprises a plurality of piezoelectric elements each having a different resonant frequency wherein an activated piezoelectric element is selected based on the size and/or girth of a user.

12. The device of claim 1 wherein said housing further comprises a biocompatible adhesive configured for affixing said device to a user.

13. The device of claim 1 further comprising a sensor module including at least one of an Electromyography (EMG) sensor or a pressure sensor.

14. The device of claim 1 wherein said housing (101) is incorporated with or provided in the form of a garment selected from the group consisting of: a diaper, underwear, belt, shirt, skirt, pant the like or any combination thereof.

15. The device of claim 1 wherein said vertical dimension (106) is adaptable with a mechanical spacer having variable size.

16. A system for determining bladder volume including the device of claim 1 and an external mobile communication device (150).

17. A processor implemented method for determining bladder volume with the device of claim 1 wherein the echo signal (104*s*) amplitude is used to determine peak to peak difference between successive peaks and wherein the difference is proportional to the instantaneous bladder volume, the method comprising:
- a) placing said device over a region overlying the urinary bladder;
- b) determining the girth of user;
- c) determining transmission frequency based on user's size and/or girth;
- d) transmitting acoustic signal at the determined transmission frequency;
- e) receiving return signal (104*s*) with at least one receiver;
- f) signal processing the received signal (104*s*) to generate an amplitude curve of said return signal (104) and to determine peak to peak difference along said curve to determine bladder volume and compared peak to peak difference with a bladder volume index to determine the bladder volume.

* * * * *